US011957441B2

(12) United States Patent
Zalevsky et al.

(10) Patent No.: US 11,957,441 B2
(45) Date of Patent: Apr. 16, 2024

(54) SYSTEM AND METHOD FOR DEPTH FLOW INSPECTION

(71) Applicant: CONTINUSE BIOMETRICS LTD., Tel Aviv (IL)

(72) Inventors: Zeev Zalevsky, Rosh HaAyin (IL); Sagi Polani, Tel-Aviv (IL); Mark Golberg, Rehovot (IL); Ran Califa, Givataym (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 743 days.

(21) Appl. No.: 17/053,261

(22) PCT Filed: Apr. 28, 2019

(86) PCT No.: PCT/IL2019/050468
§ 371 (c)(1),
(2) Date: Nov. 5, 2020

(87) PCT Pub. No.: WO2019/215717
PCT Pub. Date: Nov. 14, 2019

(65) Prior Publication Data
US 2021/0068675 A1     Mar. 11, 2021

Related U.S. Application Data

(60) Provisional application No. 62/669,451, filed on May 10, 2018.

(51) Int. Cl.
*A61B 5/026*     (2006.01)
*A61B 5/02*      (2006.01)
*A61B 5/0285*    (2006.01)

(52) U.S. Cl.
CPC ........ *A61B 5/0261* (2013.01); *A61B 5/02007* (2013.01); *A61B 5/0285* (2013.01)

(58) Field of Classification Search
CPC .. A61B 5/0261; A61B 5/02007; A61B 5/7246
See application file for complete search history.

(56) References Cited

U.S. PATENT DOCUMENTS 5,899,861 A * 5/1999 Friemel ............... G01S 7/52074
                                                     600/443
6,535,835 B1 * 3/2003 Rubin ................. G01S 15/8959
                                                     702/159

(Continued)

FOREIGN PATENT DOCUMENTS

WO    2009/013738 A1    1/2009
WO    2017/203525 A1    11/2017

OTHER PUBLICATIONS

Duncan, et al., Can laser speckle flowmetry be made a quantitative tool?, J. Opt Soc Am A Opt Image Sci Vis., Aug. 2008, pp. 2088-2094, vol. 25(8).

(Continued)

*Primary Examiner* — Oommen Jacob
(74) *Attorney, Agent, or Firm* — BROWDY AND NEIMARK, P.L.L.C.

(57) ABSTRACT

The present invention relates to a novel optical approach based on spatial analysis of spatial laser speckle patterns for tissue in-depth flow inspection characteristics. In particular, the invention relates to a technique for determining flow characteristics and identifying low blood flow or a blockage in blood vessels.

12 Claims, 10 Drawing Sheets

(56) References Cited

U.S. PATENT DOCUMENTS

| | | | |
|---|---|---|---|
| 2002/0091320 A1* | 7/2002 | Crutchfield | G01S 15/8979 600/454 |
| 2002/0183601 A1 | 12/2002 | Tearney et al. | |
| 2008/0287808 A1 | 11/2008 | Tearney et al. | |
| 2013/0144137 A1* | 6/2013 | Zalevsky | A61B 5/0066 600/314 |
| 2016/0353997 A1* | 12/2016 | Yodh | A61B 5/14553 |
| 2021/0068675 A1* | 3/2021 | Zalevsky | A61B 5/02007 |

OTHER PUBLICATIONS

Golberg, et al., In Depth Flow Inspection based on Spatial Analysis of Dynamic Laser Speckle, 2018 Conference on Lasers and Electro-Optics (CLEO), OSA, May 13, 2018, pp. 1-2.

Zimnyakov, et al., Abstract Only, Blood microcirculation monitoring by use of spatial filtering of time-integrated speckle patterns: potentialities to improve the depth resolution, Proceedings—Optical Diagnostics and Sensing of Biological Fluids and Glucose and Cholesterol Monitoring, Jun. 13, 2001, p. 1, vol. 4263.

\* cited by examiner

SYSTEM AND METHOD FOR DEPTH FLOW INSPECTION

TECHNOLOGICAL FIELD

The present invention relates to a system and method for depth flow inspection based on spatial analysis of laser speckle.

BACKGROUND ART

References considered to be relevant as background to the presently disclosed subject matter are listed below:
[1] D. D. Duncan and S. J. Kirkpatrick, "Can laser speckle flowmetry be made a quantitative tool?", J. Opt. Soc. Am. A/Vol. 25, No. 8/August 2008.
[2] D. A. Zimnyakov and A. B. Mishin, "Blood microcirculation monitoring by use of spatial filtering of time-integrated speckle patterns: potentialities to improve the depth resolution", Proc. SPIE 4263, Optical Diagnostics and Sensing of Biological Fluids and Glucose and Cholesterol Monitoring, (13 Jun. 2001).
[3] US 2002/183601
[4] US 2008/287808

Acknowledgement of the above references herein is not to be inferred as meaning that these are in any way relevant to the patentability of the presently disclosed subject matter.

BACKGROUND

In recent years, numerous studies concerning tissue microfluidic assessment have been presented. Common methods include laser Doppler velocimetry, and fluctuation analysis of speckle patterns.

Atherosclerosis is a vascular or chronic inflammatory disease associated with the development of atherosclerotic plaque or atheroma, made up of macrophages and lipids, within vessel walls. Atherosclerosis remains the leading cause of death in industrialized societies, including the US. It represents a systemic disease affecting the vessel walls of all the major arteries, including the aorta, coronary, carotid, and peripheral arteries, and leads to a myriad of diseases, including stroke, myocardial infarction, peripheral vascular disease, aortic aneurysms, and sudden death. Accurate in vivo tracking of progressive lesions would be extremely useful clinically to determine the status of patients' atherosclerotic disease. Angiography, which images the entire vessel lumen, but not the vessel wall, has historically been used to suggest the diagnosis of atherosclerosis. Areas of neovascularization, microvessel growth, endothelial permeability, and others may be indicated by various targeting agents using angiography. Magnetic resonance (MR) angiography may be used in carotid arteries and aorta to show the accumulation of carotid plaque macrophages. However, MR angiograms using gadolinium contrast agents are inadequate to show atheroma or plaque in the smaller vessels of patients such as coronary arteries or veins, for example. This inadequacy is due to the limitations on resolution and detail from MR imaging of gadolinium agents in the vascular system. Intravascular ultrasound is a catheter-based technique which produces tomographic two-dimensional cross-sectional images of vessel wall architecture and plaque and allows to discern plaque components accurately, but it is an invasive procedure and is associated with procedure-related complications. In addition, the ability of intravascular ultrasound to image the vessel wall downstream from a stenosis is limited. Furthermore, because of its high cost, intravascular ultrasound is not suitable for screening purposes in an asymptomatic population. X-ray, MR, and computed tomography (CT) angiography are likewise inadequate for confident distinction of atheroma or arterial thickening from atherosclerosis in a single imaging evaluation. This is due to also due to the inability to distinguish between normal and abnormal structures indicated, as well as the background noise of blood in the imaged vessels.

There is a need for alternative methods for detecting atheroma in a patient, particularly for the early detection of atherosclerosis before symptoms occur or the onset of advanced atherosclerotic disease.

GENERAL DESCRIPTION

The present invention provides a novel optical approach based on spatial analysis of spatial laser speckle patterns for tissue in-depth flow inspection characteristics. In particular, the invention relates to a technique for determining flow characteristics and identifying low blood flow or a blockage in blood vessels. The technique of the present invention provides an ability to capture information relating to flow in deep layers in the inspected sample/tissue. According to one aspect of the present invention, there is provided spatial analysis of the statistics of the dynamic speckle pattern generated by a laser point illumination to gain tissue depth information. The technique utilizes determining the change in the peak correlation value between each spatial point of a spatial speckle pattern from a sequence of collected secondary speckle patterns and a reference (i.e. the first) collected secondary speckle pattern in the time domain. The change in the peak correlation value (and position in some cases) might also be calculated between different wavelengths of a spatial speckle pattern. The decay time provides information on the flow characteristics in deep layers. The technique provides a spatial analysis of such collected secondary speckle pattern to provide data indicative of the in-depth flow characteristics.

Therefore, according to a broad aspect of the present invention, there is provided a system for determining flow characteristics of an object. The system comprises a processing unit adapted for receiving a plurality of sequential secondary speckle patterns originated from at least a portion of the object by a diffusive electromagnetic beam reflected from the object after being illuminated by an illumination source being placed at a certain distance from a surface of the object, processing the speckle data, wherein the processing of the speckle data comprises generating speckle data, calculating a decorrelation decay time between each spatial point of the speckle data as a function of a distance from an illumination source, performing a statistical analysis of the spatial speckle data in a time-domain and generating statistical decorrelation data thereof being indicative of the flow characteristics of the object at different layers.

In some embodiments, the technique utilizes determining (e.g. processing/calculating) the decorrelation decay time versus the distance from illumination (e.g. by determining the correlation coefficient (r) for each radius along the speckle pattern corresponding to a speckle formed from light with different sample penetration depth) and selecting a type of statistics of autocorrelation. A statistical distribution matching is then performed for the decorrelation time versus the distance from the point of illumination of the laser to show how this is occlusion and perfusion dependent.

More specifically, the processing unit is adapted for performing a statistical distribution matching of the decorrelation decay time as a function of a distance from the illumination source. The processing unit is adapted for dividing a dynamic speckle data into a plurality of time slices and calculating an autocorrelation function of each time slice. The processing unit may be adapted for fitting a different statistical model to the autocorrelation function of each time slice as a function of flow characteristics of the object at different layers. The processing unit may be adapted for fitting a statistical model of a Lorentzian linewidth with an exponential decaying decorrelation statistical model, for a Brownian motion. Also, the processing unit may be adapted for fitting a statistical model of a deviation from an exponential decaying decorrelation statistical model as a function of flow dynamics and characteristics of the object at different layers.

For example, a statistical model of the exponential decay is fitted to the obtained autocorrelation function obtained. For example, the invention provides different statistics matching the exponential graph of temporal autocorrelation decay as a result of the direct flow of particles (directional flow motion vs. non-ordered Brownian motion of particles in tissue). The inventors have found that to obtain accurate flow properties of the object at different layers, a complex statistical model that also contains a Gaussian split should be applied instead of using the exponential model of temporal autocorrelation resulting from the physics of Brownian motion. A statistical distribution matching is performed for the decorrelation time versus time to show the non-stationarity feature of the process and its ergodic properties.

In this connection, it should be understood that the inventors have shown that the analysis of the statistics provides a measure of a different motion profile of the particles, (not just according to the Brownian model which leads to an exponential division of autocorrelation), in combination with another model (e.g. of laminar particle movement where autocorrelation statistics are not exponential). The processing unit may be adapted for comparing graphs having different exponential decay coefficients as a function of flow speed. For example, gradients with different exponential decay coefficients may be compared (reference is made to the entire movement as a phonetic).

In some embodiments, properties such as flow orientation and speed are estimated. More specifically, estimation of flow speed is performed by statistical analysis of the back scattered light, with the notion that each spatial region of interest (ROI) matches a different layer along the depth axis of the phantom. The processing unit may be configured and operable for estimating at least one of relative speed of flow and flow direction. The processing unit may be also configured and operable for identifying a blockage in blood vessels.

In some embodiments, the system further comprises an imaging device unit configured for collecting at least one back scattered electromagnetic beam from the object. Alternatively, the imaging device may be configured for performing defocused imaging of at least a portion of the object to thereby collect the plurality of sequential secondary speckle patterns.

In some embodiments, the system further comprises an illumination source configured for illuminating at least a portion of the object.

According to another broad aspect of the present invention, there is provided a method for determining flow characteristics of an object. The method comprises receiving a plurality of sequential secondary speckle patterns originated from at least a portion of the object by diffusive electromagnetic beam reflected from the object after being illuminated by an illumination source being placed at a certain distance from a surface of the object; processing the speckle data to divide the sequential secondary speckle patterns into a plurality of time slices; calculating a decorrelation decay time between each spatial point as a function of a distance from the illumination source; performing a statistical analysis of the spatial speckle data in a time-domain; and generating statistical decorrelation data thereof being indicative of the flow characteristics of the object at different layers.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
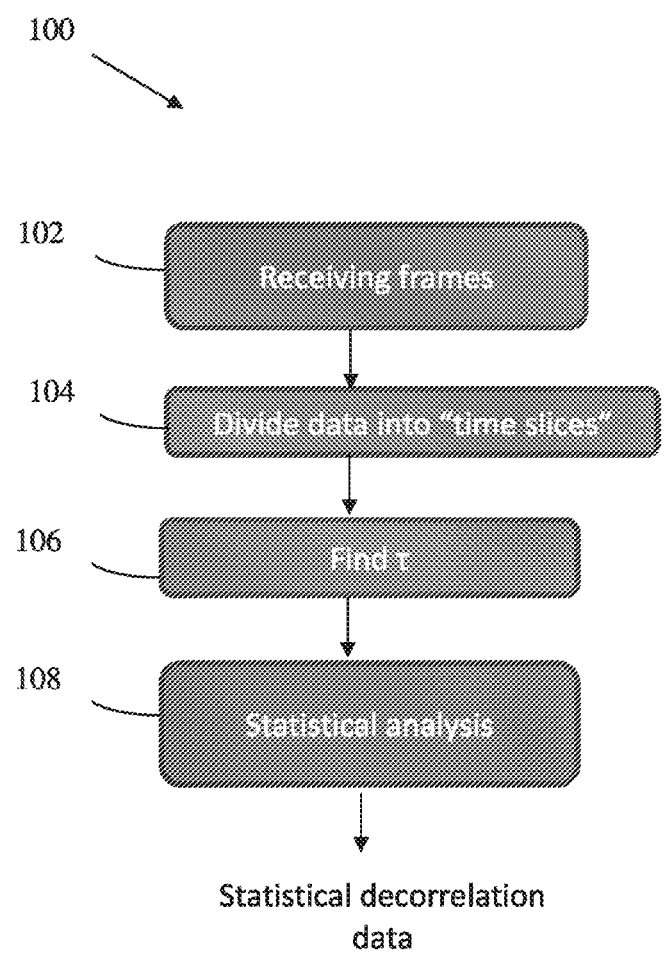
FIG. 1A is a schematic block representation of a flow chart illustrating the method of the present invention.

Certain processing steps are described and a particular order of processing steps is disclosed; however, the sequence of steps is not limited to that set forth herein and may be changed as is known in the art, with the exception of steps or acts necessarily occurring in a certain order. Reference is made to FIG. 1A, showing a flow chart illustrating the method 100 for determining flow characteristics of an object. The flow chart or any process or method described herein in other manners may represent a module, segment, or portion of code that comprises one or more executable instructions to implement the specified logic function(s) or that comprises one or more executable instructions of the steps of the progress. Although the flow chart shows a specific order of execution, it is understood that the order of execution may differ from that which is depicted. For example, the order of execution of two or more boxes may be scrambled relative to the order shown. According to one aspect of the present invention, there is provided a novel optical method for in-depth flow estimation based on dynamic speckle statistics analysis. In the present invention, the flow estimation is performed at a certain distance from the object by using a non-contact (non-invasive) technique. The proposed method is based on calculating the decorrelation decay time r, from each spatial point of the secondary speckle pattern created by diffusive light, reflected from the sample surface after illumination by a point source laser. Generally, the speckle-based monitoring techniques utilize correlation between different speckle patterns. The time dependent speckle fluctuations can be determined by calculating the autocorrelation function g2(t):

$$g_2(t) = \left\langle \frac{\langle I(t_0)I(t_0+t)\rangle}{\sqrt{\langle I(t_0)^2\rangle \langle I(t_0+t)^2\rangle}} \right\rangle,$$

where I is the intensity field of each collected speckle pattern, t, is certain time/frame, and t is a difference between two frames being correlated. The speckle pattern generally decorrelates (reduces in correlation) overtime, where a decorrelation time constant, t, can be determined. Typically, the decorrelation time is determined by fitting a single exponential function. More specifically, a spatial correlation function between successively sampled frames (images) is determined. The correlation function typically has a Gaussian-like spatial profile and can therefore be described by a "correlation peak" whose temporal variations correspond to a change in the speckle pattern over time. This may be a change in a position (shift) of the speckle pattern in the detector plane causing the change in the spatial position of the correlation peak (the shift of the speckle pattern in time shifts also the obtained spatial correlation peak), and/or a change in the shape or distribution of the speckle pattern causing the change in the correlation peak value. The method 100 comprises receiving and storing in 102 a recorded video of a plurality of sequential secondary speckle patterns and diving the recorded video into a plurality of time-wise slices in 104. In 106, for each "time-slice" an autocorrelation function is calculated and the decay decorrelation time r is extracted. A statistical analysis is then performed in 108 to generate statistical decorrelation data. Analyzing time-domain dynamic speckle statistics from the scattering sample in 108 comprises providing information regarding the motion of particles inside the medium. The inventors have found that while dynamic laser speckle reflected from particles experiencing Brownian motion can be defined by Lorentzian linewidth with an exponential decaying decorrelation statistical model, an organized particles motion (laminar flow for example) fits a different statistical model and hence a deviation from the exponential model may be formed. In the present invention, in-depth information of scatter dynamics inside the sample is achieved by analyzing speckle dynamics from different areas on the sample surface formed by diffusive light coming from different depth regions.

Figure 1B:
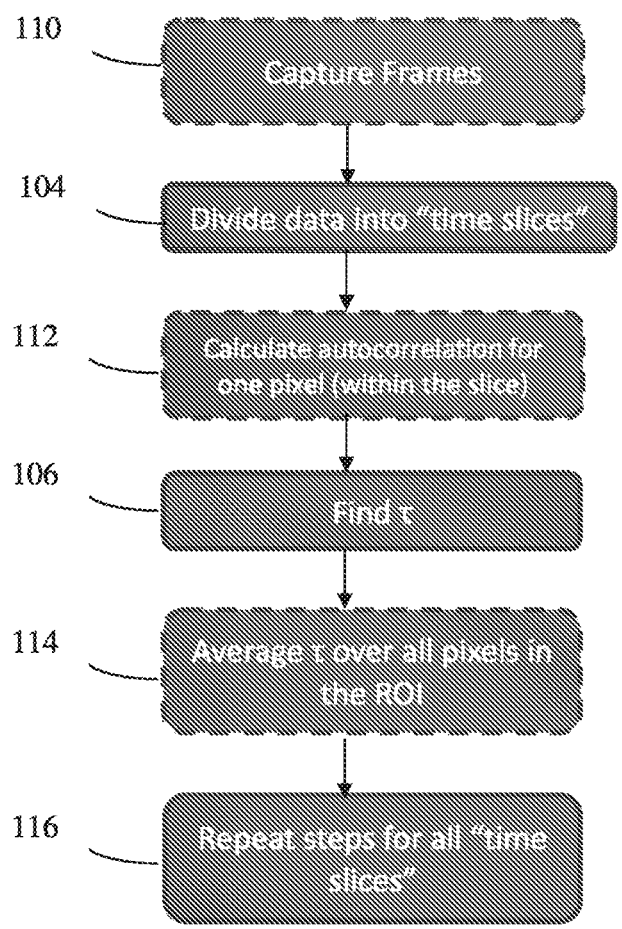
FIG. 1B is a schematic block representation of a possible flow chart illustrating the method according to some embodiments of the present invention.

Reference is made to FIG. 1B, illustrating a possible flow chart for determining flow characteristics of an object according to some embodiments of the present invention. The method 100 may comprise in 110 capturing frames of (e.g. a plurality of sequential secondary speckle patterns originated from at least a portion of the object by diffusive electromagnetic beams reflected from the object after being illuminated by an illumination source being placed at a certain distance from a surface of the object) by performing defocused imaging of at least a portion of the object. For example, 10,000 frames may be captured at a period of 1000 frames per second during 10 seconds. Calculating a decorrelation decay time τ described in FIG. 1A above may comprise calculating an autocorrelation function of each time slice in 112.

One time slice may be for example a period of 100 msec corresponding to about 100 frames. The autocorrelation function is then calculated for one pixel and the decorrelation time is then extracted for one pixel, for one time slice. The autocorrelation function may be normalized and interpolated to extract the decorrelation decay time τ. The decorrelation decay time τ can be then averaged over all the pixels in the selected region of interest. Procedures 112, 106 and 114 can be repeated for all time slices as shown in 116. The autocorrelation calculation can also be implemented in a Fourier domain using the relations between the power spectrum of the time series speckle intensity and the autocorrelation of that signal.

Figure 2A:
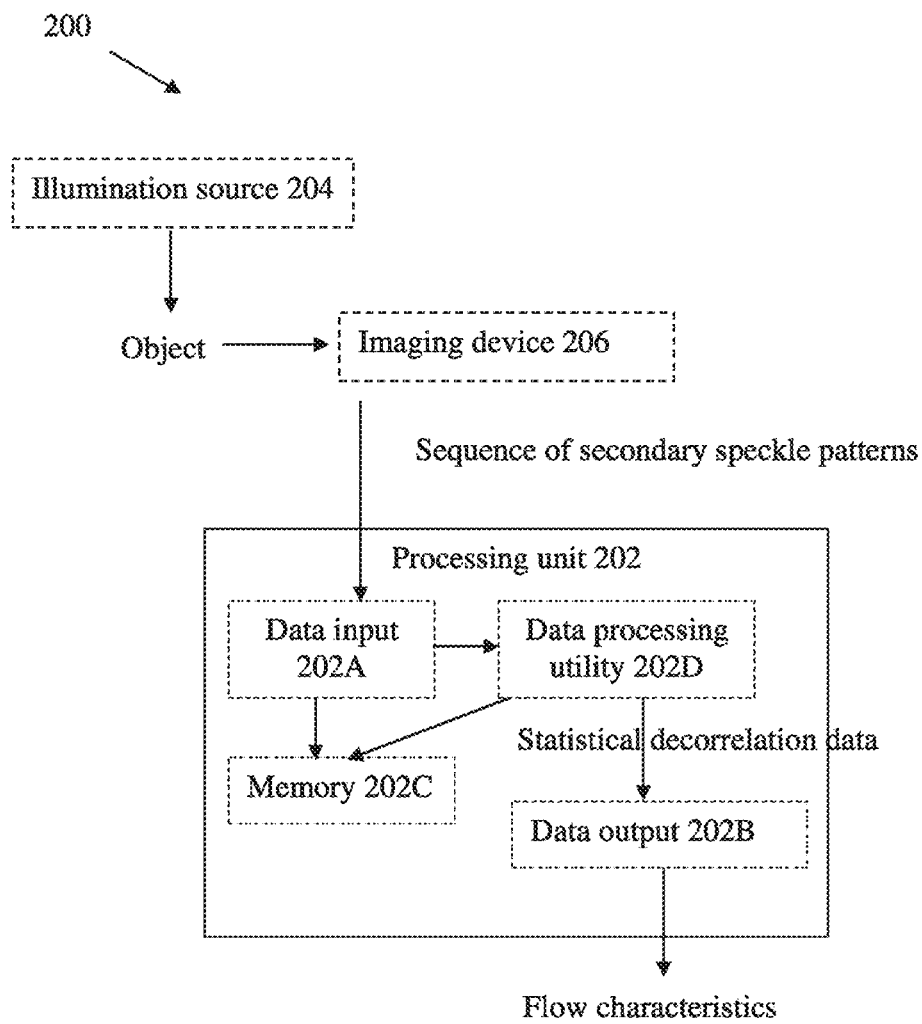
FIG. 2A is a block diagram illustrating the principal elements of the system of the present invention.

Reference is made to FIG. 2A, showing a block diagram of a system, generally designated 200, configured and operable according to the invention for determining flow characteristics of an object. An illumination source 204 may be placed at a certain distance from a surface of an object for illuminating at least a portion of an object. The illumination source 204 is a source of coherent light (e.g. laser source) being capable of emitting an electromagnetic beam in a continuous way, or in a pulsed manner A plurality of sequential secondary speckle patterns are originated from at least a portion of the object by diffusive electromagnetic beams reflected from the object. The system 200 comprises a processing unit 202 preprogrammed for processing the speckle data, performing a statistical analysis of the spatial speckle data in a time-domain, and generating statistical decorrelation data thereof being indicative of the flow characteristics of the object at different layers. The speckle data is measured data in the form of a sequence of speckle patterns generated by an imaging device being indicative of an optical response of a portion of the subject's body to illumination by coherent light according to a certain sampling time pattern. The decorrelation decay time τ may be calculated by dividing the dynamic speckle data into a plurality of time slices and calculating an autocorrelation function of each time slice. The processing unit 202 is configured generally as a computing/electronic utility including inter alia such utilities as data input and output utilities 202A, 202B, memory 202C, and data processing utility 202D. The data input utility 202A is configured for receiving speckle data. The data processing utility 202D is adapted for analyzing the speckle data, and generating output data comprising flow characteristics of the object at different layers. The memory 202C (i.e. non-volatile computer readable medium) may be adapted for storing one or more predetermined statistical models and/or a database i.e. preselected data indicative of the statistical decorrelation data versus the flow characteristics of the object. The database may be implemented with Microsoft Access, Cybase, Oracle, or other suitable commercial database systems. The processing unit 202 may be a part of and connected to a computer network. The processing unit 202 may be configured in a cloud based configuration and/or utilize Internet based computing so that parts of processing unit, and/or memory may reside in multiple distinct geographic locations.

The system 200 may be connectable (via wires or wireless signal transmission) to an imaging device 206 (e.g. PDA (pixel detector array)) for performing imaging of at least a portion of the object to thereby collect the plurality of sequential secondary speckle patterns. More specifically, the processing unit 202 is connectable via wires or wireless signal transmission (e.g. RF, IR, acoustic) to the output of the imaging device 206, and, in some applications, the same or additional control unit may include an illumination controller for selecting appropriate wavelength(s) for illumination.

In some embodiments, the imaging device 206 is a part of the system 200 and is selectively operable to provide an unfocused/defocused image of the object in the object plane, collect a sequence of secondary speckle patterns and determine at least one shift between regions of the object which appear in the sequence of secondary speckle patterns, to thereby provide motion data indicative of motion of the object along a tilt dimension and image data in an x-y plane. The sequence of secondary speckle patterns is focused on a plane displaced from the moving object. The speckle pattern method is based upon temporal tracking of a secondary reflected speckle by imaging the speckle through properly defocused optics. The tilting changes of the object surface reflect the movement of the speckle pattern in the x-y plane. In this specific case, the spatial image space transformation is a Fourier transformation (far field defocused imaging) which converts tilting changes into movement of the speckle patterns. In some embodiments, the imaging device may utilize a polarizer filter configured for blocking light components associated with specular reflection to thereby collect light components associated with scattering of light from the inspection region. The imaging device 206 may be a motion measurement system, configured in a generally similar manner to that of the above-indicated PCT Patent Publication number WO 2009/013738.

As described above, the processing unit 202 extracts the decorrelation decay time $\tau$ from the speckle data. In some embodiments, the processing unit 202 generates dynamic speckle data and calculates a decorrelation decay time $\tau$ between each spatial point of the dynamic speckle data as a function of a distance from an illumination source. In this connection, it should be noted that when the decorrelation time $r$ is obtained from a system having an imaging device 206 performing defocused imaging to thereby provide motion data indicative of motion of the object along a tilt dimension and not from a linear movement, the decorrelation time $\tau$ may be extracted due to different components of movement (translation and tilting) enhancing accuracy of the measurement. It should be understood that these types of measurements are significantly motion dependent. If the object is a part of a human body (e.g. a finger) which is moving, a lot of noise is added to the measurement. The defocusing technique enables to extract movement not due to the flow, and to subtract such movement from the decorrelation function and improve the dynamic speckle data. The present invention thus enables to perform movement cancelation providing better results in sense of sensitivity and SNR.

In some embodiments, processing unit 202 performs the statistical analysis of the spatial speckle data in a time-domain by performing a statistical distribution matching of the decorrelation decay time $\tau$ as a function of a distance from the illumination source 204. The statistical distribution matching may comprise fitting a different statistical model to the autocorrelation function of each time slice as a function of flow characteristics of the object at different layers. The statistical model may comprise a statistical model of a Lorentzian linewidth with an exponential decaying decorrelation statistical model, for a Brownian motion. Alternatively, the statistical model may comprise a statistical model of a deviation from an exponential decaying decorrelation statistical model as a function of flow dynamics and characteristics of the object at different layers. Statistical analysis of the spatial speckle data in a time-domain may comprise comparing graphs having different exponential decay coefficients as a function of flow speed. The processing unit 202 is adapted for estimating at least one of relative speed of flow and flow direction of the flow within the object. In particular, processing unit 202 may identify blockage in blood vessels.

Figure 2B:
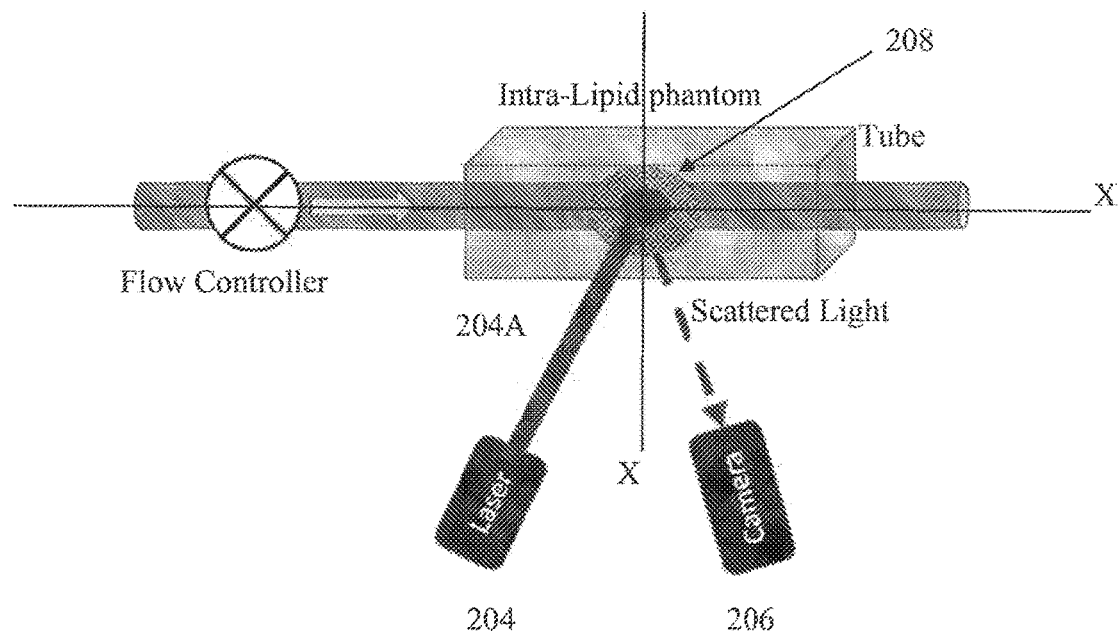
FIGS. 2B-2C show possible implementations of the system according to some embodiments of the present invention.

Reference is made to FIG. 2B showing an experimental set-up implementing the novel technique of the present invention. The technique was tested on phantoms (i.e. intra-lipid phantom) simulating tissue with a blood vessel connected to a flow controller. The source of coherent light 204 emits a light beam 204A to illuminate a certain region of interest in the object 208 during a certain time period (continuously or by multiple timely separated sessions). The object constitutes a body region of a subject (e.g. individual) whose movement is affected by a change in the body condition, typically a flow of a fluid of interest (i.e. a fluid having a property that is to be measured). The object's diffusive surface responds to coherent illumination by a speckle pattern which propagates toward the imaging device 206 and is captured during the certain time period, to generate output measured data. More specifically, the in-vitro experiment includes a sample simulating scattering tissue and a mixture of Intralipid and Agarose with a plastic tube inserted through its center. The sample was illuminated by a green laser source 104 (532 nm, 30 mW) with a spot diameter of 1 mm, while video of the dynamic laser speckle pattern was captured by a high-speed camera 106 at 100 Kfps (Photron Ax-200).

Figure 2C:
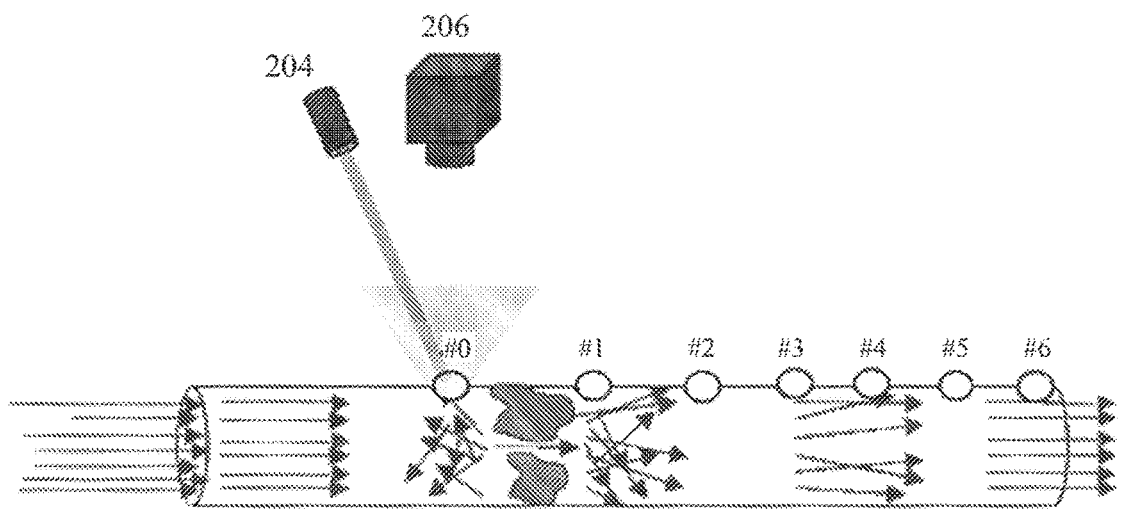

FIG. 2C shows inspection of several regions of interest along the X axis of the object. A laser 204 illuminates sequentially different regions of interest designated as #0-#6 and the electromagnetic beam scattered from each region interest is sequentially collected by the imaging device 206 (e.g. camera) being sequentially displaced relatively to the object. Several parameters were extracted, e.g. orientation and relative speed of the flow. The processing unit correlates the decay time with the velocity of the flow.

In case of flow velocity, the measurement can be carried out in one of two possible ways. In a first method, measurement of the temporal profile may be simultaneously performed at two (or more) spatial positions with a known distance between them. By correlating the temporal sequence of pulses extracted from the two spatial positions, the temporal relative shift between the two sets of pulses may be computed. This temporal shift when dividing by the a priori known spatial distance between the two measurement points, provides the flow velocity. In a second method, measurement of the flow velocity can be carried out by doing only one measurement in a single spatial location. In this case the exact temporal profile of the pulsation is measured at high temporal resolution (with a fast detector at a sampling rate of e.g. GHz). Since the flow velocity affects the flow profile along the blood artery as explained above, high precision extraction of the temporal pulsation profile can be related to the flow velocity.

Figure 3:
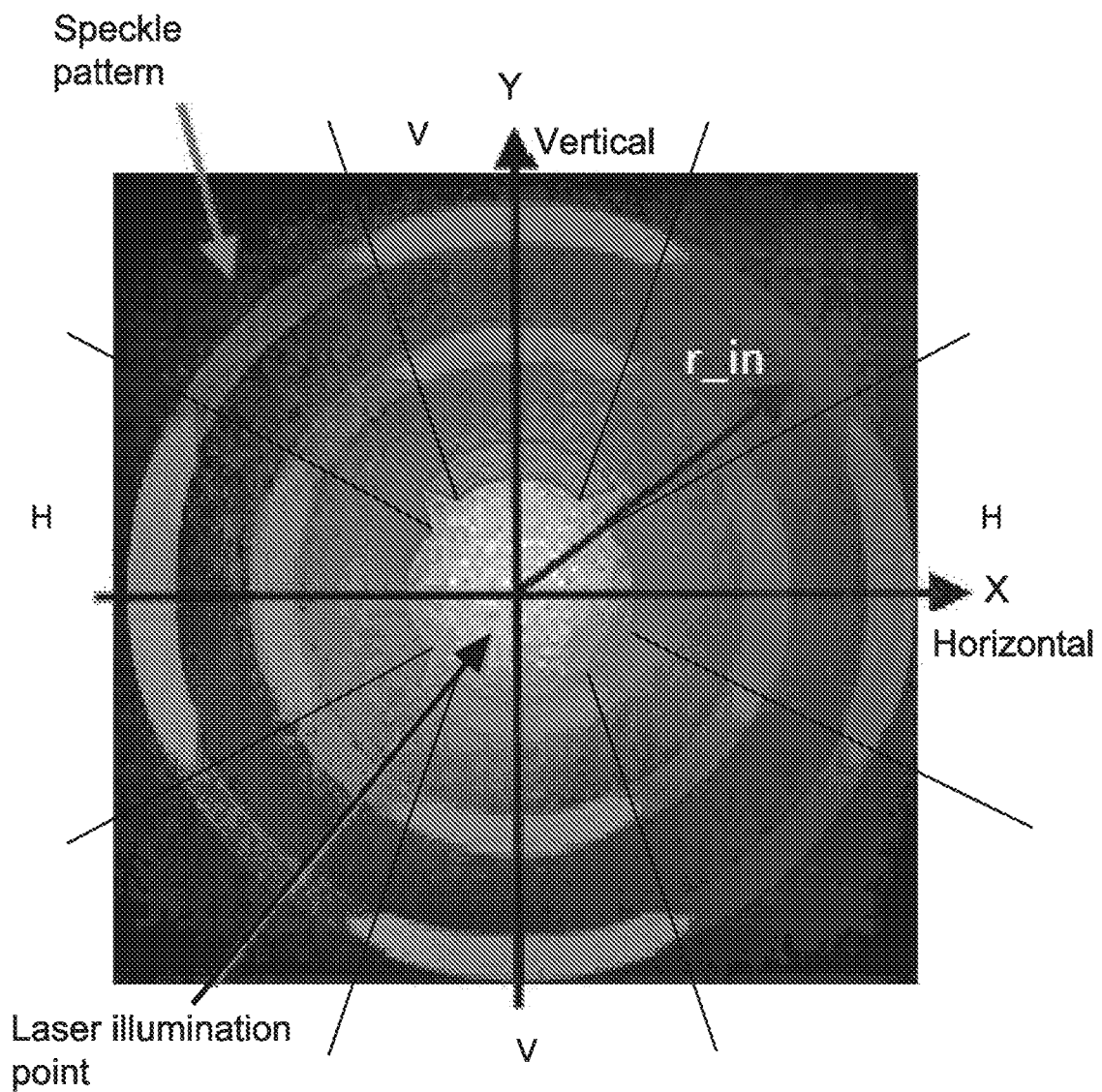
FIG. 3 shows a secondary speckle pattern on a circular shaped grid as a function of the distance from the laser illumination point.
Figure 4A:
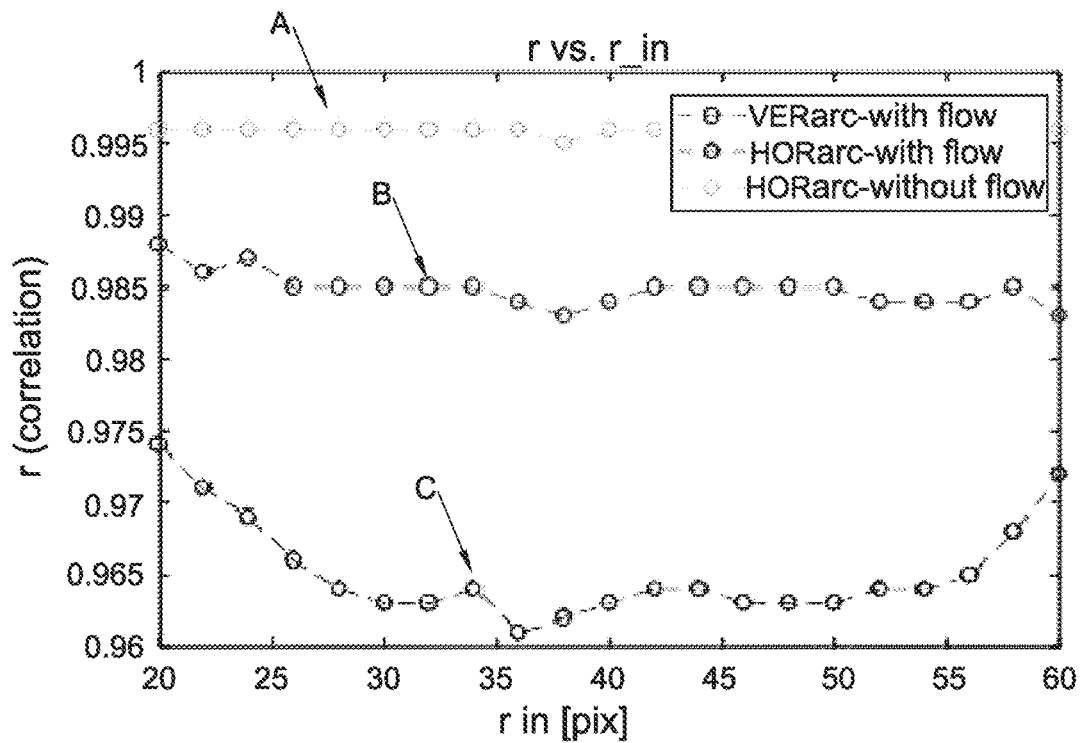
FIG. 4A shows graphs of the correlation coefficient (r) for each radius indicative of different flow states.

Reference is made now to FIG. 3 showing a two-dimensional illustration of the speckle pattern obtained by the system of FIG. 2B. In this specific and non-limiting example, the processing unit 202 of FIG. 2A has processed the speckle data and has selected a circular shaped grid to display the analysis of the spatial dynamic-laser pattern. The processing unit 202 has calculated the autocorrelation function as described above, and has fitted a statistical model of the exponential decay to the autocorrelation function. To gain phantom in depth information, inspection of circular patterns with an increasing diameter was used. In FIG. 3, the laser illumination point is located in the center of the picture (coordinates 0,0). Each arc (radius) corresponds to a speckle formed from light with different sample penetration depth. The processing unit is adapted for fitting a different statistical model to the autocorrelation function of each time slice as a function of flow characteristics of the object at different layers. For each different radius (r_in) being indicative of the distance between the laser and the different layers of the phantom, the processing unit has calculated a correlation coefficient r(correlation). The three rings of FIG. 3 correspond to three different regions of interest (ROIs) along the depth axis (Y axis) of the phantom. The first ring near the center represents the tissue region, while the third ring represents the blood vessels region. The analysis of each ring provides an analysis of blood flow in the different layers of the object. The autocorrelation decay time may be calculated by performing a correlation between the pixels for each ring. For the sake of comparison, the experiments were performed twice, with flow or without flow. The processing unit has performed a statistical analysis of the spatial speckle data by fitting the statistical model to a statistical model of a deviation from exponential decay statistics. The results are shown in FIG. 4A representing different graphs A, B and C of a correlation coefficient r (correlation) for each radius along the speckle pattern. The X axis represents the radius in pixels, while the Y axis represents the fitting match parameter to exponential model (1=100% match). Curve A shows the correlation coefficient for the horizontal portions (designated as H shown along the X axis in FIG. 3) without flow. This graph is as a reference to obtain a standard deviation (Std) measurement, and is equal to 5.1e-4. Curve B shows the correlation coefficient for the vertical portions (designated as V shown along the Y axis in FIG. 3) with flow. Curve C shows the correlation coefficient for the horizontal portions with flow. As can be clearly seen, the correlation coefficient of curve B is higher than curve C. Therefore, differentiation between vertical portions and horizontal portions was observed. As expected, since tube orientation was horizontal, when there is a flow in the tube, the horizontal portions of the circular ROIs behave differently versus the vertical ones. As may also be clearly seen, the correlation coefficient of curve C is lower than that of curve A. Therefore, differentiation between with flow and without flow states was also observed. Curve C, which is of lower magnitude (1e-2) than curve A, is assumed to be the result of the flow dynamics. It can also be observed that the decorrelation decay time decreases when the change in the speckle data is faster being indicative of an increase of the flow motion. As described above, the processing unit correlates the decay time with the velocity of the flow.

Figure 4B:
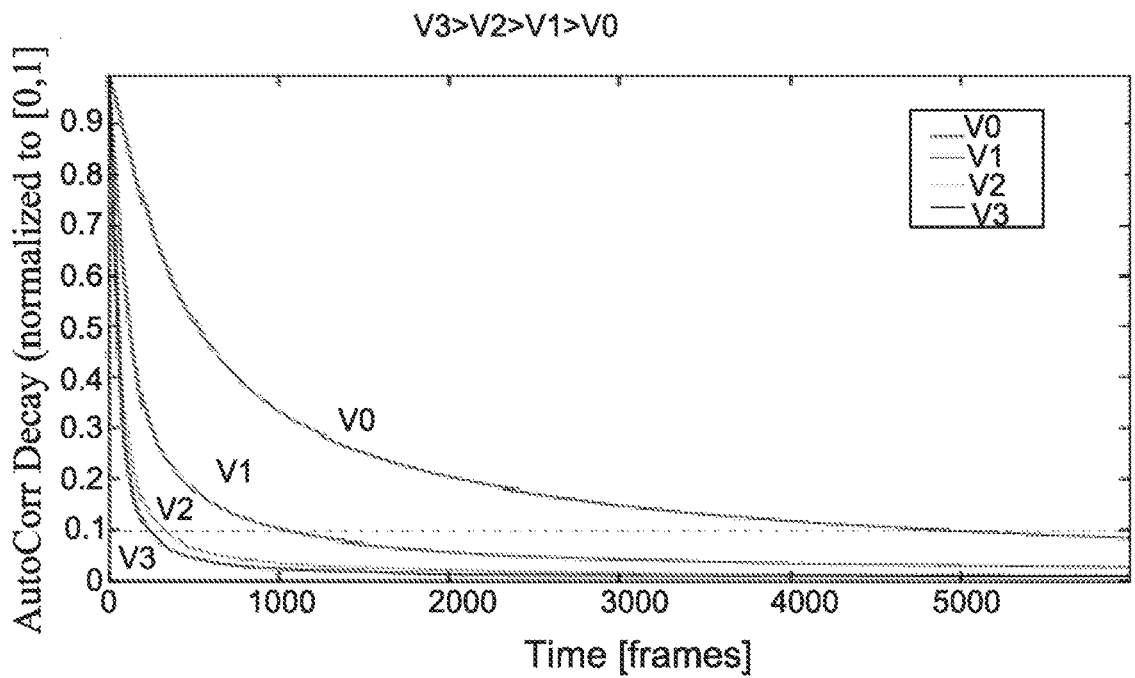
FIG. 4B shows a decay curve as a function of various flow speeds.

For the sake of comparison, the tube was connected to an external pump allowing controlled flow of Intralipid solution at four distinct velocities (V0-V3). The processing unit has performed a statistical analysis comparing the different exponential decay coefficients. The results are shown in FIG. 4B showing normalized autocorrelation decay time as a function of time. The dependence of different velocities on the autocorrelation decay time and the effect of various flow speeds on the decay distribution are clearly shown. Such different exponential decay coefficients are indicative of different flow speeds and different flow characteristics. The correlation between the exponential decay coefficients and the flow characteristics may be stored in a database as described above. The processing unit is configured and operable for identifying flow speed and/or different flow characteristics based on the exponential decay coefficients. It can be clearly seen from the figures that the autocorrelation decay time fits a different statistical model, as compared for example to FIG. 6 below.

These graphs demonstrate that the technique of the present invention is capable of distinguishing between ROIs in which there is a flow, and ROIs in which there is no flow. Moreover, the direction of the flow motion and the estimation of the flow velocity can also be estimated by using the technique of the present invention.

Figure 5:
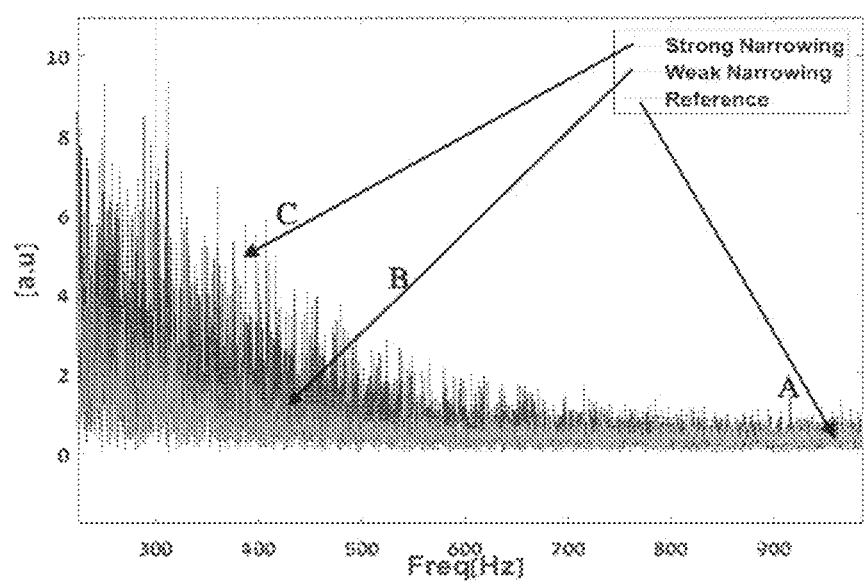
FIG. 5 shows experimental results indicative of different flow states as compared to a reference signal.

In the experimental set-up of FIG. 2B, the inventors narrowed the internal volume tube at two different sizes, and the processing unit calculated the autocorrelation decay time according to the technique of the present invention for the different states. Reference is made to FIG. 5 showing the decay decorrelation time as a function of the frequency for three different states of the tube. Curve A represents a reference state in which the internal diameter of the tube was not narrowed. Curve B represents a state in which the internal diameter of the tube was narrowed to a certain size. Curve C represents a state in which the internal diameter of the tube was narrowed to a higher degree (i.e. a smaller diameter). It is therefore clearly shown from the results that the technique of the present invention enables to detect different narrowing states of a tube being indicative of, for example, atherosclerosis and blood occlusion. Therefore, the present invention provides a novel non-invasive optical measurement technique for determining atherosclerosis or blood occlusion. The results presented in FIG. 5, were carried out with a system having an imaging device performing defocused imaging to thereby provide motion data indicative of motion of the object along a tilt dimension. This approach enables to exploit the mechanical vibration spectrum of the tube. In this connection, it should be noted that the speckle data may be processed for generating dynamic speckle data using a regular imaging device configured for collecting at least one back scattered electromagnetic beam from the object. Alternatively, a defocus imaging of the light returning from the sample may be performed, to thereby provide image data corresponding to a secondary speckle pattern of scattered light. In this case, the acquisition of the speckle provides a speckle pattern tracking done by computing the position and not only the value of the obtained correlation peak. As described above, these types of measurements are significantly motion dependent. If the object is a part of a human body (e.g. a finger) which is moving, a lot of noise is added to the measurement. The defocusing technique enables to extract movement not due to the flow, and to subtract such movement from the decorrelation function, and improves the dynamic speckle data. The present invention thus enables to perform movement cancelation providing better results in sense of sensitivity and SNR. The decorrelation time r may then be extracted due to different components of movement (translation and tilting) enhancing accuracy of the measurement. The processing of the speckle pattern comprises an acoustic vibrational analysis correlated to different flow profiles. Therefore, the different time patterns having a specific signature, as represented for example in each one of curves A-B, may be correlated to specific different flow profiles. The correlation between different acoustical vibration spectrums and different flow profiles may be stored in a database to enable the processing unit to determine a flow profile based on an acoustical vibration spectrum pattern.

Figure 6:
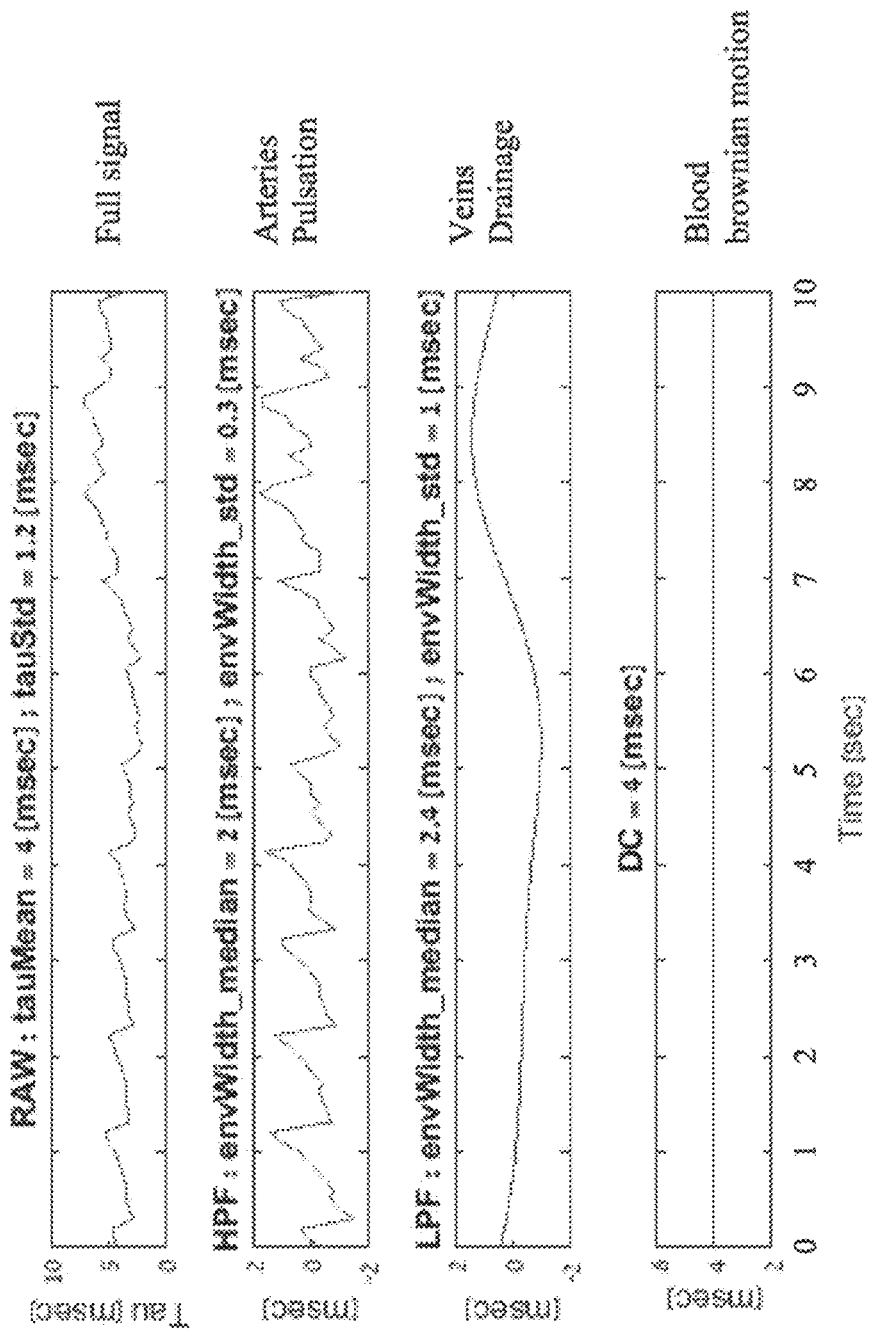
FIG. 6 shows experimental results comparing the decorrelation time for different blood vessel types.

The inventors also conducted different experiments calculating the decay decorrelation time for in vivo tissue (i.e. a human foot). Reference is made to FIG. 6 simulating different states of the blood vessels. The different spectral components were analyzed to reveal different blood flow patterns. For example, it has been shown that the upper frequencies relate to arterioles blood pulsation, while the low frequencies relate to venule blood flow followed by a vasoconstriction mechanism. The DC components relates to mechanical tissue properties (intracellular and intercellular fluids). It is clearly therefore shown that analysis of the decorrelation time enables to distinguish between different blood vessels such as arteries and veins.

Figure 7:
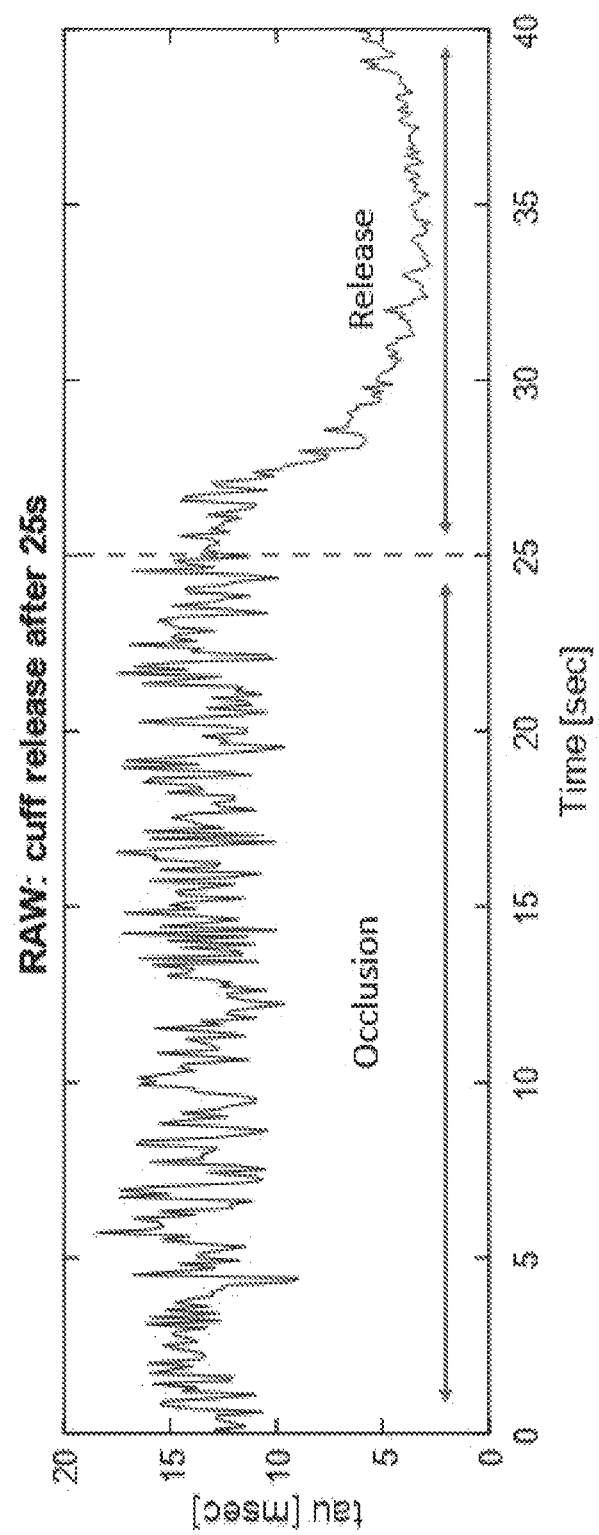
FIG. 7 shows experimental results showing cuff occlusion dependence of the decorrelation time.

The inventors also conducted different experiments on a patient's leg in vivo calculating the decay decorrelation time for different occlusion states. A cuff was placed on the lower portion of a tibia of a subject occluding arterial blood flow for a certain period of time of 25 seconds. Thereafter, the occlusion was released. The processing unit calculated the decorrelation time as a function of time. The results are shown in FIG. 7. It is clearly shown that analysis of the decorrelation time enables to distinguish between different occlusion states. Such a decay decorrelation pattern indicative of an occlusion state may be stored in a database, as described above. The processing unit is configured and operable for identifying such patterns of the decorrelation decay time, and to identify therefrom blockage in blood vessels. Moreover, it can be noted that the results show different non exponential statistics as compared for example to the results shown in FIG. 4B.

Figure 8A:
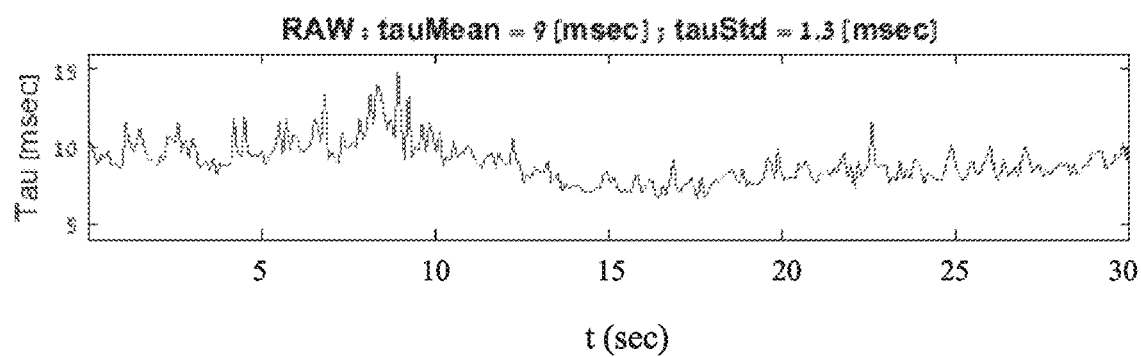
FIGS. 8A-8B show experimental results comparing the decorrelation time for different illumination wavelengths.
Figure 8B:
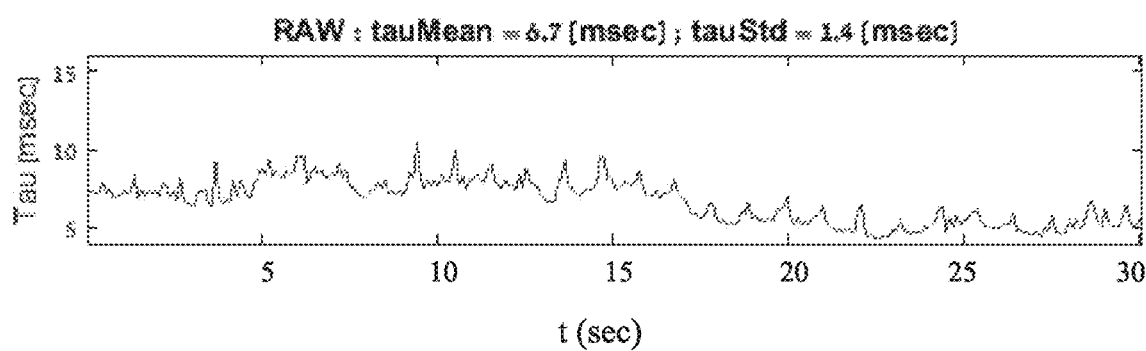

The inventors also conducted different experiments calculating the decay decorrelation time for different wavelengths of the illumination source. The results are shown in FIG. 8A and FIG. 8B. FIG. 8A shows a decorrelation decay time measured as a function of time for an illumination source having a wavelength of 650 nm. FIG. 8B shows a decorrelation decay time of the same for an illumination source having a wavelength of 940 nm. Due to the historical emphasis on pulse oximetry, the wavelengths usually selected for pulse oximetry are red (650 nm) and/or infra-red (940 nm). The results show different penetration lengths due to wavelength dependent absorption of the tissue.

The invention claimed is:

1. A system for determining flow characteristics of an object, the system comprising a processing unit adapted for receiving and processing recorded video including a plurality of sequentially sampled frames from the object being illuminated, said processing comprising:
   dividing the recorded video, comprising a plurality of secondary speckle patterns originated from at least a portion of the object, into a plurality of time-wise slices,
   calculating autocorrelation function for pixels in the frames of the time-wise slices and extracting a decorrelation decay time for each of said time-wise slices and for each of said pixels, corresponding to each spatial point of said plurality of secondary speckle patterns, as a function of a distance from a point of illumination, corresponding to a penetration depth of the illumination at said spatial point, and
   based on the decorrelation decay time, performing a statistical analysis of the plurality of secondary speckle patterns in a time-domain and generating statistical decorrelation data thereof being indicative of the flow characteristics of the object at different penetration depths of said illumination, thereby enabling to identify low blood flow or a blockage in blood vessels.

2. The system of claim 1, wherein said processing unit is adapted for carrying out at least one of the following: performing a statistical distribution matching of said decorrelation decay time as the function of the distance from the point of illumination; fitting a different statistical model to said autocorrelation function of each time slice as a function of flow characteristics of the object at different penetration depths; fitting a statistical model of a Lorentzian linewidth with an exponential decaying decorrelation statistical model, for a Brownian motion; fitting a statistical model of a deviation from an exponential decaying decorrelation statistical model as a function of flow dynamics and characteristics of the object at different penetration depths; comparing graphs having different exponential decay coefficients as a function of flow speed; estimating at least one of relative speed of flow and flow direction or identifying a blockage in blood vessels.

3. The system of claim 2, further comprising an imaging device unit configured for collecting back scattered light from the object in response to the illumination, to thereby collect said plurality of sequential secondary speckle patterns.

4. The system of claim 3, wherein said imaging device is configured for performing defocused imaging of at least a portion of the object to thereby collect said plurality of sequential secondary speckle patterns.

5. The system of claim 1, further comprising an illumination source configured to provide said illumination of the at least a portion of the object.

6. A method for determining flow characteristics of an object, the method comprising:
   receiving data indicative of recorded video of a plurality of sequentially sampled frames from the object being illuminated, said data comprising a plurality of sequential secondary speckle patterns originated from at least a portion of the object by diffusive electromagnetic beam reflected from the object;
   processing the plurality of sequential secondary speckle patterns, said processing comprising:
   dividing said sequential secondary speckle patterns into a plurality of time-wise slices;
   calculating autocorrelation function for pixels in the frames of the time-wise slices and extracting a decorrelation decay time for each of said time-wise slices and for each of said pixels, corresponding to each spatial point of said plurality of secondary speckle patterns, as a function of a distance from a point of illumination, corresponding to a penetration depth of the illumination at said spatial point;
   based on the decorrelation decay time, performing a statistical analysis of the plurality of secondary speckle patterns in a time-domain; and
   generating statistical decorrelation data thereof being indicative of the flow characteristics of the object at different penetration depths of said illumination, thereby enabling to identify low blood flow or a blockage in blood vessels.

7. The method of claim 6, wherein said performing the statistical analysis comprises performing statistical distribution matching of said decorrelation decay time as a function of said distance.

8. The method of claim 7, wherein said performing the statistical distribution matching comprises fitting a selected statistical model to said autocorrelation function of each time slice as a function of flow characteristics of the object at different penetration depth.

9. The method of claim 7, wherein said performing the statistical distribution matching comprises utilizing a statistical model of a Lorentzian linewidth with an exponential decaying decorrelation statistical model, defining a Brownian motion experienced by dynamic secondary speckles reflected from particles in said at least portion of the object.

10. The method of claim 7, wherein said performing the statistical distribution matching comprises utilizing a statistical model of a deviation from an exponential decaying decorrelation statistical model as a function of flow dynamics and characteristics of the object at different penetration depths.

11. The method of claim 6, wherein said statistical analysis comprises comparing graphs having different exponential decay coefficients as a function of flow speed.

12. The method of claim 6, wherein said processing further comprises at least one of the following estimating at least one of relative speed of flow and flow direction; identifying a blockage in blood vessels; providing said data indicative of the recorded video by performing defocused imaging of at least a portion of the object or by collecting at least one back scattered electromagnetic beam from the object.

* * * * *